(12) United States Patent
Tanahashi et al.

(10) Patent No.: US 9,353,217 B2
(45) Date of Patent: May 31, 2016

(54) BIODEGRADABLE PARTICLES, VASCULAR OCCLUSION MATERIAL, AND METHOD FOR PRODUCING BIODEGRADABLE PARTICLES

(75) Inventors: Kazuhiro Tanahashi, Otsu (JP);
Megumi Nakanishi, Otsu (JP);
Yasufumi Yamamura, Otsu (JP);
Masaki Fujita, Otsu (JP)

(73) Assignee: Toray Industries, Inc. (JP)

( * ) Notice: Subject to any disclaimer, the term of this patent is extended or adjusted under 35 U.S.C. 154(b) by 422 days.

(21) Appl. No.: 13/991,495

(22) PCT Filed: Dec. 9, 2011

(86) PCT No.: PCT/JP2011/078510
§ 371 (c)(1),
(2), (4) Date: Jun. 4, 2013

(87) PCT Pub. No.: WO2012/077776
PCT Pub. Date: Jun. 14, 2012

(65) Prior Publication Data
US 2013/0253136 A1    Sep. 26, 2013

(30) Foreign Application Priority Data

Dec. 9, 2010  (JP) ................................. 2010-274312

(51) Int. Cl.
*C08G 65/332*  (2006.01)
*C08G 65/00*  (2006.01)
*A61L 31/14*  (2006.01)
*C08J 3/12*  (2006.01)
*C08J 3/24*  (2006.01)
*A61L 24/00*  (2006.01)
*A61L 24/04*  (2006.01)

(52) U.S. Cl.
CPC ............. *C08G 65/00* (2013.01); *A61L 24/0031* (2013.01); *A61L 24/0042* (2013.01); *A61L 24/046* (2013.01); *A61L 31/14* (2013.01); *A61L 31/148* (2013.01); *C08G 65/332* (2013.01); *C08G 65/3322* (2013.01); *C08J 3/12* (2013.01); *C08J 3/24* (2013.01); *A61L 2300/60* (2013.01); *A61L 2430/36* (2013.01); *C08G 2650/30* (2013.01); *C08J 2300/16* (2013.01)

(58) Field of Classification Search
CPC .......................... C08G 65/332; C08G 65/3322
USPC .................................................. 525/61, 328.8
See application file for complete search history.

(56) References Cited

FOREIGN PATENT DOCUMENTS

| EP | 0 092 918 | 11/1983 |
|---|---|---|
| JP | 05-000969 A | 1/1993 |
| JP | 5-17245 | 1/1993 |
| JP | 05-017245 B2 | 1/1993 |
| JP | 2004-167229 A | 6/2004 |
| JP | 2005-312623 A | 11/2005 |
| JP | 2005-314535 | * 11/2005 |
| JP | 2005-314535 A | 11/2005 |
| JP | 2006-508710 A | 3/2006 |
| JP | 2007-145826 A | 6/2007 |
| JP | 2007-146146 A | 6/2007 |
| JP | 2007-291323 A | 11/2007 |
| WO | 2006/016600 A1 | 2/2006 |

* cited by examiner

*Primary Examiner* — Edward Cain
(74) *Attorney, Agent, or Firm* — DLA Piper LLP (US)

(57) ABSTRACT

Spherical biodegradable particles have improved flexibility, cause less aggregation among particles, and have improved particle shape-recovering ability after passing through a catheter or the like. The biodegradable particles include a synthetic polymer chemically cross-linked to a polyvalent carboxylic acid, the biodegradable particles having a water content of 20 to 90% in a water-saturated state.

8 Claims, No Drawings

BIODEGRADABLE PARTICLES, VASCULAR OCCLUSION MATERIAL, AND METHOD FOR PRODUCING BIODEGRADABLE PARTICLES

TECHNICAL FIELD

This disclosure relates to biodegradable particles, a vascular embolization material, and a method for producing biodegradable particles.

BACKGROUND

As materials for embolizing blood vessels and the like for the purposes of hemostasis upon incision of an affected area, blocking the nutrient supply to a tumor, maintenance of the concentration of an anticancer drug in a tumor, etc., polymer particles such as cross-linked acrylic particles, degradable starch particles, poly(lactic acid/glycolic acid)copolymers (JP 05-000969 A) and block copolymers of polyethylene glycol and polylactic acid (JP 05-017245 B2, JP 2004-167229 A, JP 2005-312623 A and JP 2007-291323 A) are widely used. Among these, to tightly and securely embolizing blood vessels and the like, spherical polymer particles are preferably used.

The above-mentioned polymer particles can be delivered through a microcatheter or the like to the target site for vascular embolization, but they have problems such as insufficient flexibility and occurrence of aggregation to cause clogging of the catheter, and irreversible deformation of the polymer particles themselves before they reach the target site.

To solve these problems, control of the elasticity of the polymer particles by blending a plurality of types of polymers (JP 2007-145826 A), improvement in the ability to pass through a catheter by covering the surfaces of polymer particles with polyethylene glycol (JP 2007-146146 A), use of chemically cross-linked polymer particles (JP 2005-314535 A) and the like have been reported, and improved technologies have been developed.

However, although improvement in the problems of controlling the elasticity of polymer particles and the ability to pass through a catheter can be seen in the improved technologies such as blending of a plurality of types of polymers (JP '826), covering of the surfaces of polymer particles (JP '146) and use of chemically cross-linked polymer particles (JP 535), improvement in the problem of irreversible deformation of polymer particles themselves is insufficient. Hence, further improvement has been demanded to attain good embolization of blood vessels and the like. That is, development of an embolization material for blood vessels and the like wherein the ability of the polymer particles to recover their original shape after passing through a catheter (hereinafter referred to as "particle shape-recovering ability") is enhanced is demanded.

Further, in improvement of a material for embolization of blood vessels and the like, conventional chemical cross-linking reactions to obtain chemically cross-linked spherical polymer particles require dispersion of a solution of a polymer or the like in a protic solvent such as water to form its droplets. However, since the protic solvent itself is involved in the chemical cross-linking reaction, control of the density of the chemical cross-links, and the like are very difficult, so that further improvement has been limited.

It could therefore be helpful to provide spherical biodegradable particles which have improved flexibility, cause less aggregation among particles, and have improved particle shape-recovering ability after passing through a catheter or the like, and a method of producing the particles.

SUMMARY

We provide biodegradable particles, vascular embolization materials and their production methods described in (1) to (14) below:

(1) Biodegradable particles comprising a synthetic polymer chemically cross-linked to a polyvalent carboxylic acid, the biodegradable particles having a water content of 20 to 90% in the water-saturated state.

(2) The biodegradable particles according to (1) above, whose compression ratio is 15 to 60% and whose recovery ratio is not less than 15% in the water-saturated state.

(3) The biodegradable particles according to (1) or (2) above, wherein the synthetic polymer is: a homopolymer or block copolymer of a water-soluble polymer(s) selected from the group consisting of polyethylene glycol, polypropylene glycol, polyvinyl alcohol, polyacrylic acid, polyhydroxyethylacrylate, polyhydroxyethylmethacrylate, polyvinylpyrrolidone, carboxymethylcellulose, hydroxymethylcellulose and hydroxyethylcellulose; or a block copolymer of the water-soluble polymer(s) and a monomer(s) selected from the group consisting of α-hydroxy acids, cyclic dimers of α-hydroxy acids, hydroxydicarboxylic acids and cyclic esters.

(4) The biodegradable particles according to (3) above, wherein the water-soluble polymer is a branched polymer in which polyethylene glycol and/or polypropylene glycol is/are bound to all hydroxyl groups in a polyalcohol.

(5) The biodegradable particles according to (4) above, wherein the polyalcohol is selected from the group consisting of glycerin, polyglycerin and pentaerythritol.

(6) The biodegradable particles according to any one of (1) to (5) above, wherein the polyvalent carboxylic acid is a dicarboxylic acid selected from the group consisting of oxalic acid, malonic acid, succinic acid, fumaric acid, glutaric acid, adipic acid, pimelic acid, suberic acid and sebacic acid.

(7) The biodegradable particles according to any one of (4) to (6) above, wherein the polyvalent carboxylic acid is a polyvalent carboxylic acid in which carboxylic groups are introduced to terminal hydroxyl groups of the branched polymer or terminal hydroxyl groups of a block copolymer of the branched polymer and a monomer(s) selected from the group consisting of α-hydroxy acids, cyclic dimers of α-hydroxy acids, hydroxydicarboxylic acids and cyclic esters.

(8) A vascular embolization material composed of the biodegradable particles according to any one of (1) to (7) above.

(9) A method for production of biodegradable particles, the method comprising:
the dissolving step wherein a synthetic polymer, polyvalent carboxylic acid and condensing agent are dissolved in an aprotic polar organic solvent having a dielectric constant of 35 to 50, to obtain Solution A;
the droplet-forming step wherein the Solution A is added dropwise to a poor solvent for the aprotic polar organic solvent, to obtain droplets of Solution A; and
the chemical cross-linking step wherein a chemical cross-linking reaction of the synthetic polymer is allowed to proceed in the droplets, to obtain biodegradable particles.

(10) The method for production according to (9) above, wherein the synthetic polymer is:
a homopolymer or block copolymer of a water-soluble polymer(s) selected from the group consisting of polyethylene glycol, polypropylene glycol, polyvinyl alcohol, polyacrylic acid, polyhydroxyethylacrylate, polyhydroxyethylmethacrylate, polyvinylpyrrolidone, carboxymethylcellulose, hydroxymethylcellulose and hydroxyethylcellulose; or
a block copolymer of the water-soluble polymer(s) and a monomer(s) selected from the group consisting of α-hydroxy acids, cyclic dimers of α-hydroxy acids, hydroxydicarboxylic acids and cyclic esters.

(11) The method for production according to (9) or (10) above, wherein the condensing agent is a water-soluble carbodiimide.

(12) The method for production according to any one of (9) to (11) above, wherein the aprotic polar organic solvent is selected from the group consisting of N,N-dimethylformamide, N,N-dimethylacetamide, acetonitrile and dimethylsulfoxide.

(13) The method for production of biodegradable particles according to any one of (9) to (12) above, wherein the poor solvent comprises a natural oil selected from the group consisting of cottonseed oil, corn oil, coconut oil, olive oil, palm oil, rapeseed oil, safflower oil, sesame oil, soybean oil, sunflower oil, turpentine oil, almond oil, avocado oil, bergamot oil, castor oil, cedar wood oil, chlorophyll oil, clove oil, croton oil, *eucalyptus* oil, fennel oil, fusel oil, grape seed oil, jojoba oil, candlenut oil, lavender oil, lemon oil, linseed oil, macadamia nut oil, meadowfoam oil, orange oil, *origanum* oil, persic oil and rose hip oil

(14) Biodegradable particles produced by: dissolving a synthetic polymer, polyvalent carboxylic acid and condensing agent in an aprotic organic solvent having a dielectric constant of 35 to 50; adding the obtained solution dropwise to a poor solvent for the aprotic polar organic solvent; and allowing a chemical cross-linking reaction to proceed in the obtained droplets.

Since the biodegradable particles have improved flexibility, cause less aggregation among the particles, and can be easily delivered to the target site in a blood vessel or the like without causing clogging of the catheter, the particles can be used as an embolization material for blood vessels and the like. Further, since the biodegradable particles have improved particle shape-recovering ability after passing through a catheter or the like, the target site can be effectively embolized, and an embolization effect corresponding to the amount of the biodegradable particles used can be expected.

DETAILED DESCRIPTION

The terms used herein are as defined below unless otherwise specified.

The biodegradable particles comprise a synthetic polymer which is chemically cross-linked to a polyvalent carboxylic acid, and have a water content of 20 to 90% in the water-saturated state.

The term "biodegradable" refers to a property of the biodegradable particles comprising a synthetic polymer chemically cross-linked to a polyvalent carboxylic acid in which they are degraded, dissolved, absorbed or metabolized in a living body, or a property of the particles in which they are excreted from inside a living body to outside the living body.

Examples of the degradation reaction include hydrolysis and enzymatic degradation. Hydrolysis is preferred since it does not depend on enzymes.

The term "chemical cross-linking" refers to a means to chemically link a synthetic polymer to a polyvalent carboxylic acid. Examples of the chemical bond for linking a synthetic polymer to a polyvalent carboxylic acid include an ester bond, thioester bond, amide bond and ureide bond. In view of increasing the biodegradability, an ester bond, thioester bond, amide bond and ureide bond are preferred.

To link a synthetic polymer to a polyvalent carboxylic acid by chemical cross-linking, the synthetic polymer needs to have two or more reactive functional groups. Examples of the "reactive functional group" herein include a carboxyl group, hydroxyl group, amino group, thiol group, isocyanate group, thioisocyanate group, glycidyl group, chlorocarbonyl group and chloroformyl group. In view of the ability to form an ester bond, amide bond or ureide bond, a hydroxyl group, carboxyl group, amino group, isocyanate group, chlorocarbonyl group and chloroformyl group are preferred.

The "polyvalent carboxylic acid" is preferably a dicarboxylic acid such as oxalic acid, malonic acid, succinic acid, fumaric acid, glutaric acid, adipic acid, pimelic acid, suberic acid, sebacic acid or tartaric acid; or a tricarboxylic acid such as malic acid; in view of the fact that these are present in the living body and highly safe. The polyvalent carboxylic acid is more preferably oxalic acid, malonic acid, succinic acid, fumaric acid, glutaric acid, adipic acid, pimelic acid, suberic acid or sebacic acid. The "polyvalent carboxylic acid" also includes, in addition to the above-described oxalic acid and the like, derivatives such as acid halides and esters corresponding to these polyvalent carboxylic acids.

Since the biodegradable particles comprise a synthetic polymer chemically cross-linked to a polyvalent carboxylic acid, the particles are water-insoluble. The term "water-insoluble" herein refers to a property in which the external appearance of the biodegradable particles does not change even in cases where the particles are immersed in water at 25° C. for 5 hours.

Examples of the "synthetic polymer" include: homopolymers and block copolymers of a water-soluble polymer(s) selected from the group consisting of polyethylene glycol (hereinafter referred to as "PEG"), polypropylene glycol (hereinafter referred to as "PPG"), polyvinyl alcohol (hereinafter referred to as "PVA"), polyacrylic acid, polyhydroxyethylacrylate, polyhydroxyethylmethacrylate, polyvinylpyrrolidone, carboxymethylcellulose, hydroxymethylcellulose and hydroxyethylcellulose; and block copolymers of the above-described water-soluble polymer(s) and a monomer(s) selected from the group consisting of α-hydroxy acids, cyclic dimers of α-hydroxy acids, hydroxydicarboxylic acids and cyclic esters.

The "water-soluble polymer" is preferably PEG, PPG, PVA, polyhydroxyethylacrylate or polyhydroxyethylmethacrylate (hereinafter referred to as "poly-HEMA") in view of the fact that they have high biocompatibility and have a hydroxyl group(s). A branched polymer in which PEG and/or polypropylene glycol is/are bound to all of the hydroxyl groups in a polyalcohol is more preferred in view of the fact that they have more hydroxyl groups. The "polyalcohol" herein is preferably glycerin, polyglycerin or a monosaccharide such as pentaerythritol.

The weight average molecular weight of the water-soluble polymer is preferably not less than 200 in view of the fact that uniform biodegradability can be obtained. Further, the weight average molecular weight is preferably not more than 50000 in view of the fact that its excretion from inside a living body to outside the living body can be easily achieved. The weight average molecular weight of the water-soluble polymer is measured under the following measurement conditions by gel permeation chromatography (hereinafter referred to as "GPC method"):

Measurement Conditions
Column: TSK gel XL series
   (7.8 mm (inner diameter)×30 cm (length); Tosoh Corporation)
Eluent: Chloroform
Column temperature: 35° C.
Flow rate: 1.0 mL/minute
Detection method: Refractive index
Calibration curve: Prepared using polystyrene standard samples The polyvalent carboxylic acid is not limited to those having a low molecular weight such as described above, and may be a polyvalent carboxylic acid in which carboxylic groups are introduced to terminal hydroxyl groups of the branched polymer described above, or a polyvalent carboxylic acid in which carboxyl groups are introduced to terminal hydroxyl groups of a block copolymer of the above-described branched polymer and a monomer(s) selected from the group consisting of α-hydroxy acids, cyclic dimers of α-hydroxy acids, hydroxydicarboxylic acids and cyclic esters.

Examples of the method for introducing carboxyl groups to terminal hydroxyl groups of the above-described branched polymer to prepare a polyvalent carboxylic acid include a method wherein succinic anhydride or glutaric anhydride is reacted with the terminal hydroxyl groups in the presence of pyridine, triethylamine or the like.

Examples of the method for reacting carboxyl groups contained in the polyvalent carboxylic acid with reactive functional groups contained in the synthetic polymer to link the synthetic polymer to the polyvalent carboxylic acid by chemical cross-linking include a method wherein carboxyl groups contained in the polyvalent carboxylic acid are reacted with hydroxyl groups contained in the synthetic polymer. The carboxyl groups are not reactive with the hydroxyl groups, but chemical cross-linking by ester bond formation can be achieved by converting the polyvalent carboxylic acid into a polyvalent carboxylic acid derivative such as a polyvalent acid halide or polyvalent ester, or by using a dehydration condensation agent.

Examples of the method of converting the polyvalent carboxylic acid into a polyvalent acid halide include a method wherein an electrophilic halogenating agent such as thionyl chloride or oxalyl chloride is reacted therewith. Examples of the dehydration condensation agent to be used to directly react the polyvalent carboxylic acid with hydroxyl groups without converting the polyvalent carboxylic acid into a derivative thereof include N,N'-dicyclohexylcarbodiimide, N,N'-diisopropylcarbodiimide and 1-ethyl-3-(3-dimethylaminopropyl)carbodiimide hydrochloride (hereinafter referred to as "EDC"). EDC is preferred in view of the fact that the reaction by-product can be easily processed.

The dehydration condensation agent may be used together with a dehydration condensation accelerator, and examples of the dehydration condensation accelerator include pyridine, 4-dimethylaminopyridine (hereinafter referred to as "DMAP") and triethylamine.

The synthetic polymer is also preferably a block copolymer wherein a water-soluble polymer block(s) is/are chemically bound to a block(s) of a biodegradable polymer such as polylactic acid. Examples of such a block copolymer include an octa-branched block copolymer (PLA×8-PEG) obtained by reacting L-lactide with an octa-branched PEG.

The weight average molecular weight of the PEG block is preferably 200 to 50000 for giving appropriate water absorbability to the biodegradable particles in the above block copolymer. Further, in order to avoid an increase in the viscosity due to gelation of the block copolymer and to give appropriate degradability to the biodegradable particles, the weight average molecular weight of the block copolymer itself is preferably 3000 to 100000. These weight average molecular weights are measured by the GPC method similarly to the weight average molecular weight of the water-soluble polymer as described above.

Examples of the method of producing the block copolymer include melt polymerization and ring-opening polymerization. Examples of the catalyst used in these polymerizations include tin halides such as tin chloride; organic acid tin salts such as tin 2-ethylhexanoate; diethyl zinc; zinc lactate; iron lactate, dimethylaluminum; calcium hydride; organic alkali metal compounds such as butyllithium and potassium t-butoxide; metal-porphyrin complexes; and metal alkoxides such as diethylaluminum methoxide.

The obtained block copolymer can be purified by, for example, fractional precipitation. More specifically, a purified block copolymer can be obtained as a precipitate by dissolving the obtained block copolymer in a good solvent for the block copolymer and then adding the resulting solution dropwise to a poor solvent in a stirred state. Further, the purity of the block copolymer can be increased by heating the poor solvent to once dissolve the precipitate and then slowly cooling the resulting solution to allow production of the precipitate again.

Examples of the good solvent used in the fractional precipitation include tetrahydrofuran, acetonitrile, dichloromethane and chloroform, and mixed solvents thereof. The amount of the good solvent to be used varies depending on the amount of the raw materials fed and the composition of the block copolymer, and is preferably an amount with which the concentration of the block copolymer dissolved therein becomes 1 to 50 wt %, more preferably 1 to 25 wt %. Examples of the poor solvent include alcohol type organic solvents and hydrocarbon type organic solvents.

The term "water-saturated state" refers to a state in which the water content of the biodegradable particles is constant when about 20 mg of the biodegradable particles are kept immersed in 10 mL of phosphate buffered saline at 37° C. (while rotating its container, a test tube, with a rotator at a rate of 0.5 rotation/second to shake the content of the test tube). The term "water content is constant" herein refers to a state in which, when the weight of the biodegradable particles immersed in phosphate buffered saline at 37° C. is measured every minute, the rate of weight change with time is within 10%. The "rate of weight change with time of the biodegradable particles" is a value calculated according to (1) below:

$$\text{Rate of weight change with time of the biodegradable particles (\%)} = \{W(t) - W(t-1)\}/W(t) \times 100 \quad (1)$$

W(t): Weight of the biodegradable particles after immersion in water for t minutes
W(t−1): Weight of the biodegradable particles after immersion in water for (t−1) minutes.

The term "water content" refers to a value calculated according to the (2) below. The term "biodegradable particles in the dry state" herein refers to the biodegradable particles immersed in deionized water at 25° C. for 3 hours and then vacuum-dried at 25° C. for 12 hours, and the term "biodegradable particles in the water-saturated state" refers to the biodegradable particles prepared by subjecting the particles to centrifugation (25° C., 1000 g×5 minutes) after the water content became constant to remove phosphate buffered saline. The water content increases when water is infiltrated into the biodegradable particles, and as the density of the chemical cross-links in the biodegradable particles increases, infiltration of water into the biodegradable particles is suppressed. That is, since the biodegradable particles show a correlation between the water content and the density of the chemical cross-links, the "water content in the water-saturated state" can be used as an indicator for measuring the degree of chemical cross-linking $$\text{Water content (\%)} = (W-W0)/W \times 100 \quad (2)$$

W: Weight of the biodegradable particles in the water-saturated state

W0: Weight of the biodegradable particles in the dry state (which should be roughly 20 mg)

In terms of the water content of the biodegradable particles in the water-saturated state, in cases where the water content is too low, the flexibility of the biodegradable particles is lost. Hence their ability to pass through a catheter decreases, while in cases where the water content is too high, the particle shape-recovering ability of the biodegradable particles is insufficient. Therefore, the water content needs to be 20 to 90%. The term "particle shape-recovering ability of the biodegradable particles" herein refers to the ability of the biodegradable particles to recover its original shape after passing through a catheter, and examples of the indicator of the ability include the recovery ratio of the biodegradable particles. The recovery ratio of the biodegradable particles can be measured under the following measuring conditions and calculated according to (3) to (5) below. $L2_a$ and $L2_b$ in (4) represent the particle diameter displacements measured in a test process wherein a compression load is gradually applied to the biodegradable particles from the minimum test force to the maximum test force, followed by reducing the load to the minimum test force. More specifically, $L2_a$ is a value representing the particle diameter displacement at the minimum test force which was initially applied to the biodegradable particles.

Measurement Conditions

Compression tester: MCT-W500 (manufactured by Shimadzu Corporation)
Test chamber temperature: 25° C.
Test chamber humidity: 50%
Particle diameter of sample: 300 to 700 μm
Upper compression indenter: Flat type, φ500 μm
Measurement mode: Loading/unloading mode
Maximum test force: 9.8 mN
Minimum test force: 0.49 mN
Loading rate: 0.8924 mN/sec.
Load retention time: 2 sec.

$$L1 = L1_b - L1_a \quad (3)$$

$L1_a$: Particle diameter displacement upon application of the minimum test force $L1_b$: Particle diameter displacement upon application of the maximum test force $$L2 = L2_b - L2_a \quad (4)$$

$L2_a$: Particle diameter displacement upon application of the minimum test force $L2_b$: Particle diameter displacement upon application of the maximum test force followed by reducing the load to the minimum test force $$\text{Recovery ratio (\%)} = (L1-L2)/d \times 100 \quad (5)$$

d: Particle diameter

Examples of the indicator of the "flexibility of the biodegradable particles" include the compression ratio of the biodegradable particles. The compression ratio of the biodegradable particles is a value measured under the same measurement conditions as in the case of the recovery ratio and calculated according to (3) above and (6) below:

$$\text{Compression ratio (\%)} = (L1/d) \times 100 \quad (6)$$

d: Particle diameter.

As the recovery ratio of the biodegradable particles increases, more accurate embolization of the target site is possible so that the recovery ratio of the biodegradable particles in the saturated state is preferably not less than 15%, more preferably not less than 25%. In cases where the recovery ratio in the water-saturated state under the measurement conditions described above is not less than 25%, the original particle diameter can be mostly regained after passing through a catheter so that there is less risk of flowing of the biodegradable particles further downstream of the target site in the blood vessel to be embolized.

Further, to obtain appropriate elasticity and ability to pass through a catheter, the compression ratio of the biodegradable particles in the water-saturated state is preferably 15 to 60%.

The average particle diameter of the biodegradable particles is preferably 20 to 2000 μm, more preferably 50 to 1500 μm in consideration of the diameter of the blood vessel as the target site for embolization. Further, it is preferred that the distribution width of the particle diameter be narrow, and the particle diameter is more preferably within the range of the average particle diameter±100 μm, still more preferably within the range of the average particle diameter±50 μm. The term "distribution width of the particle diameter" herein refers to the range of the particle diameter in which the diameters of not less than 99% of all particles are included. The particle diameter of the biodegradable particles for medical use can be measured by the light scattering method.

The shape of the biodegradable particles is preferably spherical at 37° C. since, in this case, the direction of the biodegradable particles hardly affects the condition of the embolus.

It is preferred that the remaining weight of the biodegradable particles in the dry state after immersion in phosphate buffered saline at 37° C. for 28 days be not more than 80%, more preferably not more than 50%, with respect to the weight of the biodegradable particles in the dry state before the immersion. Further, it is still more preferred that the remaining weight of the biodegradable particles in the dry state after immersion in phosphate buffered saline at 37° C. for 7 days be not more than 50% with respect to the weight of the biodegradable particles in the dry state before the immersion.

Our biodegradable particles can be used to embolize a blood vessel. In such a case, the biodegradable particles may be used as they are, or may be dispersed in an appropriate dispersion medium or contrast medium before use.

Examples of the dispersion medium described above include vegetable oils such as sesame oil and corn oil; and distilled water for injection. The distilled water for injection may be supplemented with a dispersant(s) such as polyoxysorbitan fatty acid ester and/or carboxymethyl cellulose; preservative(s) such as methylparaben and/or propylparaben; isotonic agent(s) such as sodium chloride, mannitol and/or glucose; antiseptic(s), stabilizer(s), solubilizer(s) and/or vehicle(s) used for injections; and/or the like.

The contrast medium described above may be either ionic or nonionic, and examples of the contract medium include IOPAMIRON (registered trademark; Schering), HEXABRIX (registered trademark; Eiken Chemical Co., Ltd.), Omnipaque (registered trademark; Daiichi Sankyo Healthcare Co, Ltd.), Urografin (registered trademark; Schering), and IOMERON (registered trademark; Eisai Co., Ltd.).

Our method of producing biodegradable particles comprises:
- a dissolving step wherein a synthetic polymer, polyvalent carboxylic acid and condensing agent are dissolved in an aprotic polar organic solvent having a dielectric constant of 35 to 50, to obtain Solution A;
- a droplet-forming step wherein the Solution A is added dropwise to a poor solvent for the aprotic polar organic solvent, to obtain droplets of Solution A; and
- a chemical cross-linking step wherein a chemical cross-linking reaction of the synthetic polymer is allowed to proceed in the droplets, to obtain biodegradable particles.

In cases where a protic solvent such as water or alcohol is used for preparation of Solution A, the protic solvent itself may be involved in the chemical cross-linking reaction, resulting in a large decrease in the density of chemical cross-links. Therefore, use of a protic solvent is not preferred.

In the "dissolving step", the aprotic polar organic solvent having a dielectric constant of 35 to 50 for dissolving the synthetic polymer, polyvalent carboxylic acid and condensing agent is preferably N,N-dimethylformamide (hereinafter referred to as "DMF"), N,N-dimethylacetamide, acetonitrile or dimethylsulfoxide (hereinafter referred to as "DMSO"), and acetonitrile is more preferred since it can be easily evaporated under reduced pressure.

The "droplet-forming step" is a step wherein the Solution A obtained in the dissolving step is added dropwise to a poor solvent in a stirred state to obtain fine droplets of Solution A by stirring shearing, thereby forming biodegradable particles as spherical particles.

The "chemical cross-linking step" is a step that proceeds in parallel with the droplet-forming step and, in this step, the chemical cross-linking reaction is allowed to proceed at the same time with the shape formation of the biodegradable particles.

The poor solvent mentioned above is preferably an oil such as a synthetic oil or natural oil, more preferably a natural oil, because, for example, aprotic polar organic solvents having a dielectric constant of 35 to 50 are not dissolved in them; their viscosity is high enough to obtain spherical biodegradable particles; sedimentation does not occur due to their high specific gravities and the stirring efficiency is therefore high; the density of the chemical cross-links can be easily controlled; and there is no need to add a surfactant since they themselves play a role as a surfactant that prevents adhesion among the droplets.

In cases where a protic solvent such as water or alcohol is used as the poor solvent, the protic solvent itself may be involved in the chemical cross-linking reaction, resulting in a large decrease in the density of chemical cross-links. Therefore, use of a protic solvent is not preferred.

Examples of the synthetic oil include silicone oil. Examples of the natural oil include cottonseed oil, corn oil, coconut oil, olive oil, palm oil, rapeseed oil, safflower oil, sesame oil, soybean oil, sunflower oil, turpentine oil, almond oil, avocado oil, bergamot oil, castor oil, cedar wood oil, chlorophyll oil, clove oil, croton oil, *eucalyptus* oil, fennel oil, fusel oil, grape seed oil, jojoba oil, candlenut oil, lavender oil, lemon oil, linseed oil, macadamia nut oil, meadowfoam oil, orange oil, *origanum* oil, persic oil and rose hip oil. Cottonseed oil, corn oil, olive oil, rapeseed oil, safflower oil, sesame oil, soybean oil and sunflower oil are preferred since they are biologically highly safe and can be stably obtained.

EXAMPLES

Our particles, materials and methods will now be described in detail by way of Examples. However, this disclosure is not limited to the Examples.

Example 1

In 50 mL of acetonitrile, 0.5 g of succinic acid (Wako Pure Chemical Industries, Ltd.), 1 mL of DMAP (Acros) and 10 g of dehydrated octa-branched PEG (SUNBRIGHT (registered trademark); average molecular weight: 20000; NOF Corporation) were dissolved to obtain the solution A-1. Fifty milliliter of the solution A-1 heated to 35° C. was taken into a syringe, and slowly added dropwise to cottonseed oil in a stirred state to obtain droplets of the solution A-1. After completion of the dropwise addition of the solution A-1, the resultant was stirred for additional 1 hour at room temperature, and the obtained droplets were collected, followed by washing the droplets with acetone and then drying the droplets under reduced pressure, to obtain biodegradable particles.

Example 2

Biodegradable particles were obtained by the same method as in Example 1 except that 0.6 g of glutaric acid (Wako Pure Chemical Industries, Ltd.) was used instead of succinic acid.

Example 3

Biodegradable particles were obtained by the same method as in Example 1 except that 0.7 g of adipic acid (Wako Pure Chemical Industries, Ltd.) was used instead of succinic acid.

Example 4

Under nitrogen flow, 3 g of L-lactide (Purac; hereinafter referred to as "LA") and 10 g of dehydrated octa-branched PEG (SUNBRIGHT (registered trademark); average molecular weight: 20000; NOF Corporation) were placed in a flask, and the resulting mixture was melt-mixed at 110° C. The mixture was then heated to 150° C., and 3 mg of tin dioctanoate (Wako Pure Chemical Industries, Ltd.) was added thereto to allow the reaction to proceed, to obtain an octa-branched block copolymer (PLA×8-PEG). The obtained octa-branched block copolymer was dissolved in dichloromethane, and the resulting solution was added dropwise to a large excess of an acetone/diethyl ether mixture, to obtain white precipitates. The weight average molecular weight of the white precipitates was found to be about 25000 as measured by the GPC method.

Under nitrogen flow, 0.5 g of succinic anhydride (Wako Pure Chemical Industries, Ltd.), 1 mL of dehydrated pyridine (Aldrich) and 10 g of dehydrated octa-branched PEG (SUNBRIGHT (registered trademark); average molecular weight: 20000; NOF Corporation) were mixed together, and allowed to react at 80° C. under reflux, to obtain PEG in which carboxyl groups were introduced to its terminal hydroxyl groups (hereinafter referred to as "carboxylated PEG"). The obtained carboxylated PEG was dissolved in dichloromethane, and the resulting solution was added dropwise to a large excess of an acetone/diethyl ether mixture, to obtain white precipitates.

The weight average molecular weight of the white precipitates was found to be about 25000 as measured by the GPC method.

In 1 mL of acetonitrile, each of 0.5 g of the octa-branched block copolymer and 0.5 g of the carboxylated PEG polymer was dissolved. From each of the resulting two solutions, a 75-μL aliquot was collected, and the aliquots were mixed together. To the resulting mixture, 10 μL of DMAP (Acros)/acetonitrile solution (2 wt %) and 5 μL of EDC (Wako Pure Chemical Industries, Ltd.) were added, to obtain the solution A-2. Fifty milliliter of the solution A-2 heated to 35° C. was taken into a syringe, and slowly added dropwise to cottonseed oil in a stirred state, to obtain droplets of the solution A-2. After completion of the dropwise addition of the solution A-2, the resultant was stirred for additional 1 hour at 35° C., and the obtained droplets were collected, followed by washing the droplets with acetone and then drying the droplets under reduced pressure, to obtain biodegradable particles.

Example 5

Biodegradable particles were obtained by the same method as in Example 4 except that DMF was used instead of acetonitrile and that olive oil was used instead of cottonseed oil.

Example 6

Biodegradable particles were obtained by the same method as in Example 4 except that DMSO was used instead of acetonitrile and that sesame oil was used instead of cottonseed oil.

Example 7

Biodegradable particles were obtained by the same method as in Example 4 except that 2 g of LA and 2 g of glycolide (Boehringer Ingelheim) were used instead of 3 g of LA.

Example 8

Biodegradable particles were obtained by the same method as in Example 4 except that 2 g of LA and 2 g of ε-caprolactone (Wako Pure Chemical Industries, Ltd.; hereinafter referred to as "CL") were used instead of 3 g of LA.

Example 9

Biodegradable particles were obtained by the same method as in Example 4 except that 10 g of PVA (Wako Pure Chemical Industries, Ltd.) was used instead of each of PEG.

Example 10

Biodegradable particles were obtained by the same method as in Example 4 except that 10 g of poly-HEMA (Polysciences, Inc.) was used instead of each of PEG.

Comparative Example 1

Biodegradable particles were obtained by the same method as in Example 1 except that dichloromethane was used as the solvent of the dispersed phase and that 5 wt % aqueous PVA solution was used instead of cottonseed oil.

Comparative Example 2

Biodegradable particles were obtained by the same method as in Example 4 except that dichloromethane was used as the solvent of the dispersed phase and that 5 wt % aqueous PVA solution was used instead of cottonseed oil.

Comparative Example 3

Biodegradable particles were obtained by the same method as in Example 4 except that 1 g of the above-described octa-branched block copolymer and 1 g of the above-described carboxylated PEG polymer were used and that the temperature of the solution to be added dropwise to cottonseed oil was 45° C.

Evaluation of Physical Properties of Biodegradable Particles

The biodegradable particles obtained in Examples 1 to 10 and Comparative Examples 1 to 3 were processed into the water-saturated state, and each of them was subjected to measurement of the compression ratio, recovery ratio and water content. The results are shown in Table 1.

Evaluation of Biodegradability of Biodegradable Particles

The biodegradable particles obtained in Examples 1 to 10 and Comparative Examples 1 to 3 were respectively immersed in phosphate buffered saline at 37° C. for 28 days, and then their weight in the dry state was measured. The ratio of the thus measured weight with respect to the weight in the dry state before the immersion (hereinafter referred to as "degradability in PBS") was calculated. The results are shown in Table 1.

TABLE 1

| | | Materials | | | Dispersed phase | | | Compression rate [%] | Recovery rate [%] | Water content [%] | Degradability in PBS [%] |
|---|---|---|---|---|---|---|---|---|---|---|---|
| | | Synthetic Polymer | Water-soluble polymer block | Monomers in biodegradable polymer block | Polyvalent carboxylic acid | Organic Solvent | Dielectric constant | Poor solvent | | | | |
| Example | 1 | Octa-branched PEG | — | — | Succinic acid | Acetonitrile | 37 | Cottonseed oil | 24 | 19 | 33 | 18 |
| | 2 | Octa-branched PEG | — | — | Glutaric acid | Acetonitrile | 37 | Cottonseed oil | 18 | 15 | 24 | 14 |
| | 3 | Octa-branched PEG | — | — | Adipic acid | Acetonitrile | 37 | Cottonseed oil | 28 | 19 | 37 | 17 |
| | 4 | Block Copolymer | Octa-branched PEG | LA | Carboxylated PEG | Acetonitrile | 37 | Cottonseed oil | 51 | 25 | 60 | 13 |

TABLE 1-continued

| | | Materials | | | Dispersed phase | | | Com-pression rate [%] | Recovery rate [%] | Water content [%] | Degrad-ability in PBS [%] |
|---|---|---|---|---|---|---|---|---|---|---|---|
| | | Synthetic Polymer | Water-soluble polymer block | Monomers in biodegradable polymer block | Polyvalent carboxylic acid | Organic Solvent | Dielectric constant | Poor solvent | | | | |
| | 5 | Block Copolymer | Octa-branched PEG | LA | Carboxylated PEG | DMF | 38 | Olive oil | 56 | 34 | 72 | 10 |
| | 6 | Block Copolymer | Octa-branched PEG | LA | Carboxylated PEG | DMSO | 47 | Sesame oil | 49 | 26 | 63 | 16 |
| | 7 | Block Copolymer | Octa-branched PEG | LA Glycolide | Carboxylated PEG | Acetonitrile | 37 | Cottonseed oil | 35 | 22 | 46 | 2 |
| | 8 | Block Copolymer | Octa-branched PEG | LA CL | Carboxylated PEG | Acetonitrile | 37 | Cottonseed oil | 58 | 78 | 85 | 15 |
| | 9 | Block Copolymer | PVA | LA Glycolide | Carboxylated PEG | Acetonitrile | 37 | Cottonseed oil | 44 | 22 | 58 | 19 |
| | 10 | Block Copolymer | Poly-HEMA | LA Glycolide | Carboxylated PEG | Acetonitrile | 37 | Cottonseed oil | 50 | 42 | 62 | 17 |
| Comparative Example | 1 | Octa-branched PEG | — | — | Succinic acid | Dichloromethane | 9 | Water | 84 | 10 | 97 | 2 |
| | 2 | Block Copolymer | Octa-branched PEG | LA | Carboxylated PEG | Dichloromethane | 9 | Water | 91 | 4 | 94 | 10 |
| | 3 | Block Copolymer | Octa-branched PEG | LA | Carboxylated PEG | Acetonitrile | 37 | Cottonseed oil | 5 | 86 | 12 | 19 |

Evaluation of Ability of Biodegradable Particles to Pass through Catheter

The 200 mg aliquots of the biodegradable particles obtained in Examples 1 to 10 were respectively dispersed in 2 mL of distilled water for injection. Each of these dispersions was injected from a syringe into a microcatheter having a total length of about 1500 mm and a tip inner diameter of 530 μm (RENEGADE; Boston Scientific). As a result, it could be confirmed that the biodegradable particles could be smoothly injected into the microcatheter without showing adhesion to the syringe wall. After the injection of the dispersion, the microcatheter was cut along the longitudinal direction to visually observe its inner surface. As a result, no residual spherical biodegradable particle was found. In terms of the particle diameters before and after passing through the catheter, all of the biodegradable particles obtained in Examples 1 to 10 had a diameter within the range of 660±80 μm before the passing and a diameter within the range of 650±90 μm after the passing. Thus, the particle diameter after the passing was not largely different from that before the passing.

INDUSTRIAL APPLICABILITY

The biodegradable particles can be used to embolize blood vessels in the medical field.

The invention claimed is:

1. A method of producing biodegradable particles comprising:
   a dissolving step wherein a synthetic polymer, polyvalent carboxylic acid and condensing agent are dissolved in an aprotic polar organic solvent having a dielectric constant of 35 to 50, to obtain Solution A;
   a droplet-forming step wherein said Solution A is added dropwise to a poor solvent for said aprotic polar organic solvent, to obtain droplets of Solution A; and
   a chemical cross-linking step wherein a chemical cross-linking reaction of said synthetic polymer is allowed to proceed in said droplets, to obtain biodegradable particles.

2. The method according to claim 1, wherein said synthetic polymer is:
   a homopolymer or block copolymer of a water-soluble polymer(s) selected from the group consisting of polyethylene glycol, polypropylene glycol, polyvinyl alcohol, polyacrylic acid, polyhydroxyethylacrylate, polyhydroxyethylmethacrylate, polyvinylpyrrolidone, carboxymethylcellulose, hydroxymethylcellulose and hydroxyethylcellulose; or
   a block copolymer of said water-soluble polymer(s) and a monomer(s) selected from the group consisting of α-hydroxy acids, cyclic dimers of α-hydroxy acids, hydroxydicarboxylic acids and cyclic esters.

3. The method according to claim 1, wherein said condensing agent is a water-soluble carbodiimide.

4. The method according to claim 1, wherein said aprotic polar organic solvent is selected from the group consisting of N,N-dimethylformamide, N,N-dimethylacetamide, acetonitrile and dimethylsulfoxide.

5. The method according to claim 1, wherein said poor solvent comprises a natural oil selected from the group consisting of cottonseed oil, corn oil, coconut oil, olive oil, palm oil, rapeseed oil, safflower oil, sesame oil, soybean oil, sunflower oil, turpentine oil, almond oil, avocado oil, bergamot oil, castor oil, cedar wood oil, chlorophyll oil, clove oil, croton oil, *eucalyptus* oil, fennel oil, fusel oil, grape seed oil, jojoba oil, candlenut oil, lavender oil, lemon oil, linseed oil, macadamia nut oil, meadowfoam oil, orange oil, *origanum* oil, persic oil and rose hip oil.

6. The method according to claim 2, wherein said condensing agent is a water-soluble carbodiimide.

7. The method according to claim 2, wherein said aprotic polar organic solvent is selected from the group consisting of N,N-dimethylformamide, N,N-dimethylacetamide, acetonitrile and dimethylsulfoxide.

8. The method according to claim 3, wherein said aprotic polar organic solvent is selected from the group consisting of N,N-dimethylformamide, N,N-dimethylacetamide, acetonitrile and dimethylsulfoxide.

\* \* \* \* \*